(12) United States Patent
Van De Veen

(10) Patent No.: US 7,001,434 B2
(45) Date of Patent: Feb. 21, 2006

(54) DEVICE FOR PIVOTABLY CONNECTING PARTS OF AN ORTHOPAEDIC DEVICE

(75) Inventor: Paul Gerard Van De Veen, Enschede (NL)

(73) Assignee: Otto Bock Austria Ges. m.b.H, Vienna (AT)

( * ) Notice: Subject to any disclaimer, the term of this patent is extended or adjusted under 35 U.S.C. 154(b) by 144 days.

(21) Appl. No.: 10/473,720

(22) PCT Filed: Mar. 30, 2002

(86) PCT No.: PCT/EP02/03588

§ 371 (c)(1),
(2), (4) Date: Oct. 1, 2003

(87) PCT Pub. No.: WO02/080825

PCT Pub. Date: Oct. 17, 2002

(65) Prior Publication Data

US 2004/0107008 A1 Jun. 3, 2004

(30) Foreign Application Priority Data

Apr. 4, 2001 (NL) .......................................... 1017771

(51) Int. Cl.
*A61F 2/64* (2006.01)

(52) U.S. Cl. .......................................... 623/39; 623/45
(58) Field of Classification Search ............. 623/39, 623/41–46
See application file for complete search history.

(56) References Cited

U.S. PATENT DOCUMENTS

| 2,667,644 | A | * | 2/1954 | Johnson ........................ 623/26 |
| 5,314,498 | A | * | 5/1994 | Gramnas ....................... 623/39 |
| 5,545,232 | A |   | 8/1996 | Van de Veen |
| 5,728,173 | A | * | 3/1998 | Chen ............................. 623/44 |
| 5,888,236 | A |   | 3/1999 | Van de Veen |
| 5,921,358 | A | * | 7/1999 | Gramnas ..................... 188/294 |

FOREIGN PATENT DOCUMENTS

| GB | 2 134 392 | 8/1984 |
| WO | WO96/07378 | 3/1996 |

* cited by examiner

*Primary Examiner*—Bruce E Snow
(74) *Attorney, Agent, or Firm*—Whitham, Curtis & Christofferson, P.C.

(57) ABSTRACT

The invention relates to a device for pivotably connecting parts of an orthopaedic device, such as in particular a prosthetic knee for leg amputees, which device comprises a kinematic multibar mechanism with at least four bars, which bar mechanism allows a movement in the walking direction (L), in which device—a first bar can be connected to a first part of the orthopaedic device, such as a thigh socket,—a second bar can be rigidly connected to a second part of the orthopaedic device, such as a lower-leg part,—a third bar, which is arranged at the front as seen in the walking direction (L), is pivotably connected to the first bar and is pivotably connected to the second bar,—a fourth bar, which is arranged behind the third bar as seen in the walking direction, is pivotably connected to the first bar and is pivotably connected to the second bar, in such a manner that the connection between the second bar and the fourth bar can be displaced along an imposed path, and—a centre part of the fourth bar, lying between the two ends of the fourth bar, being connected to the third bar, in such a manner that the connection between the third bar and the centre part can be displaced along an imposed path.

15 Claims, 7 Drawing Sheets

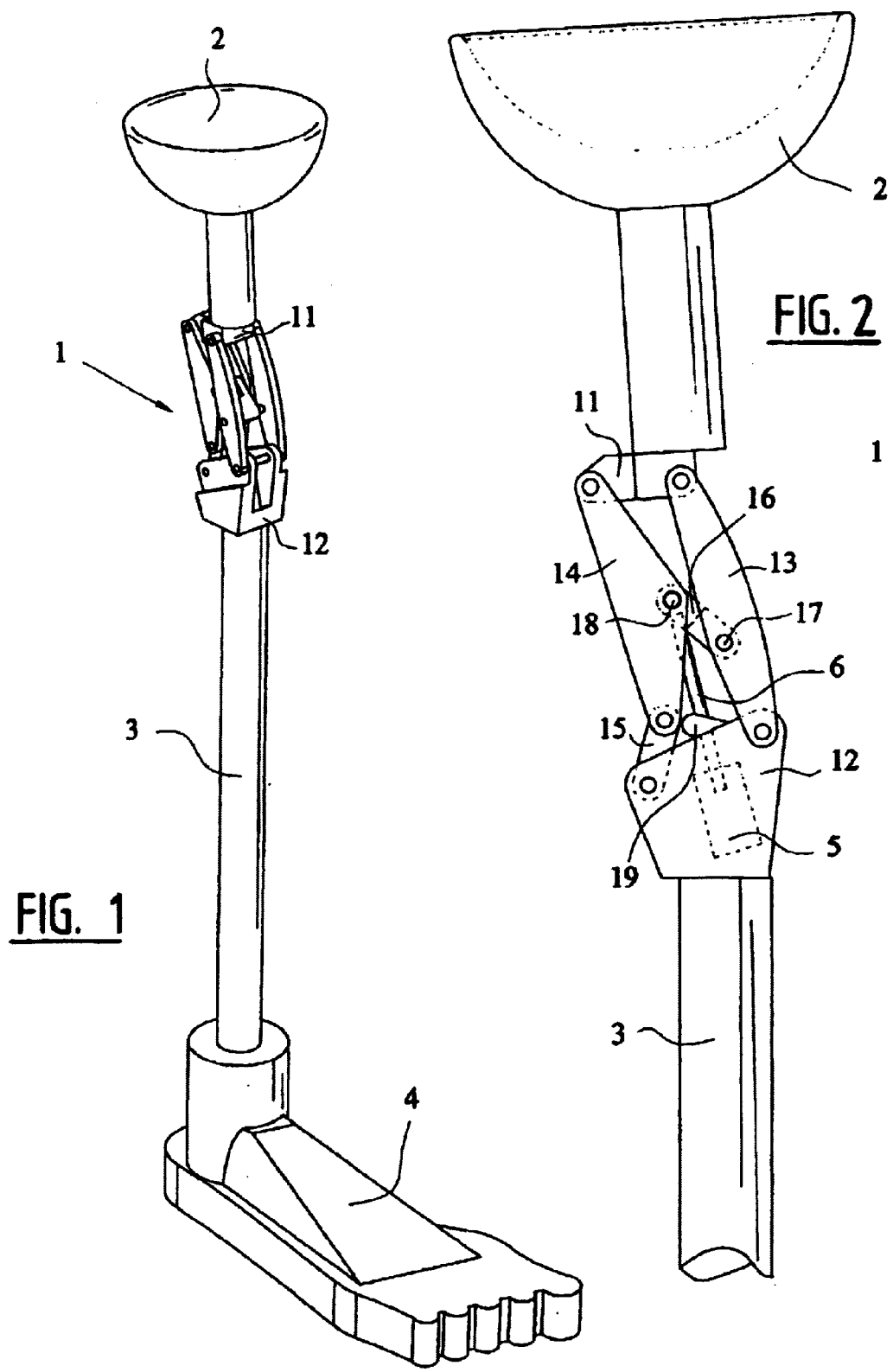

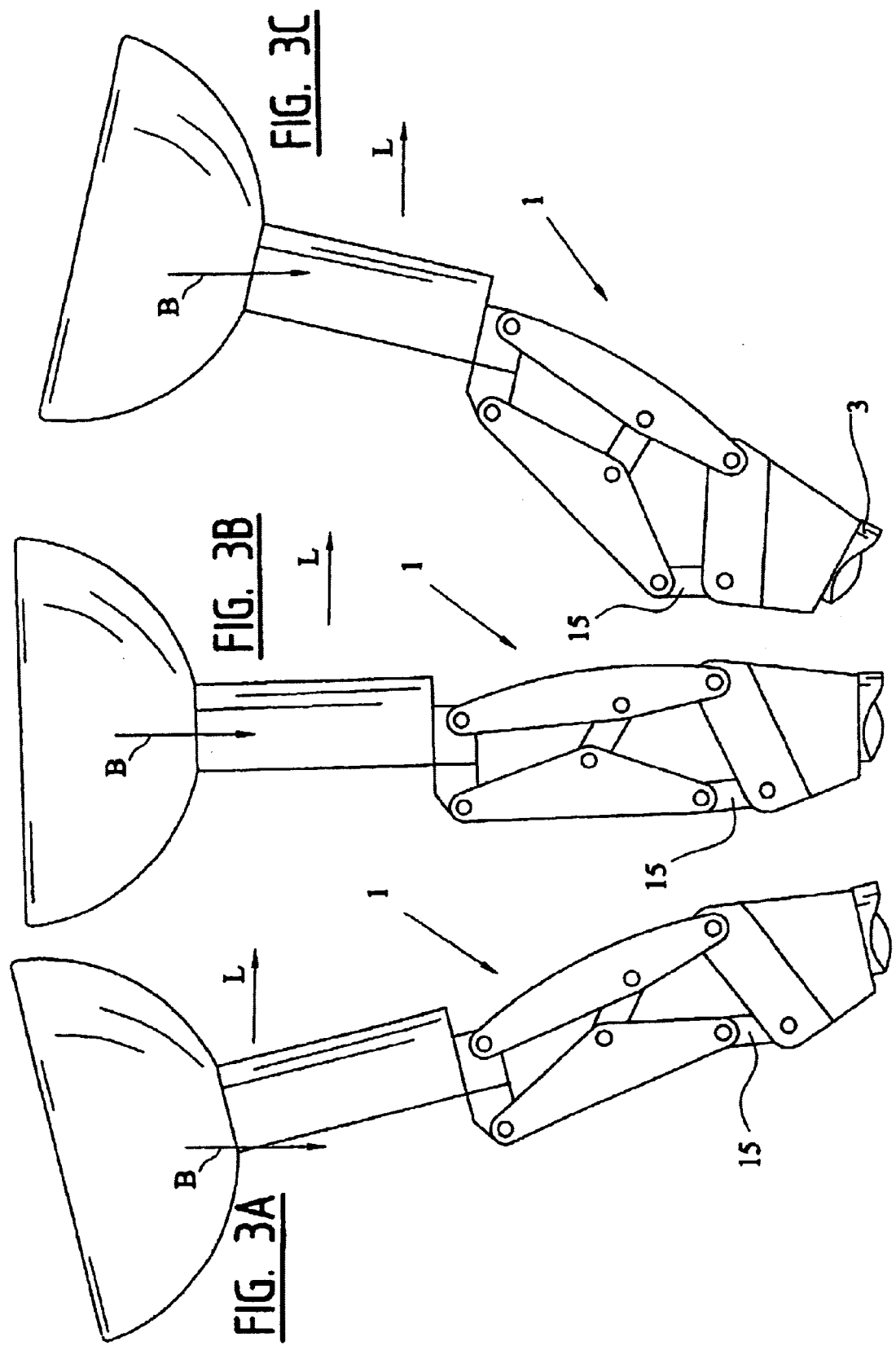

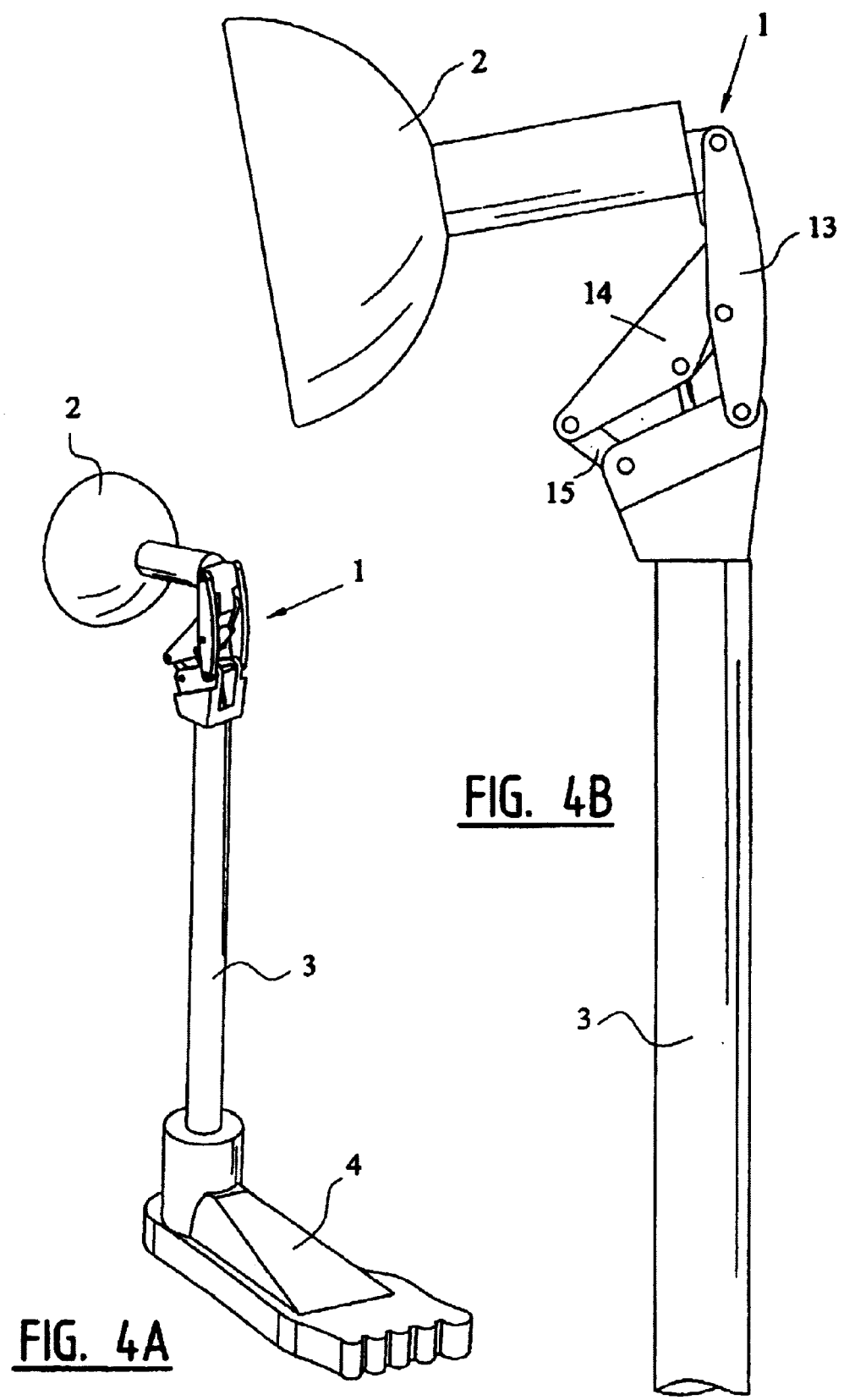

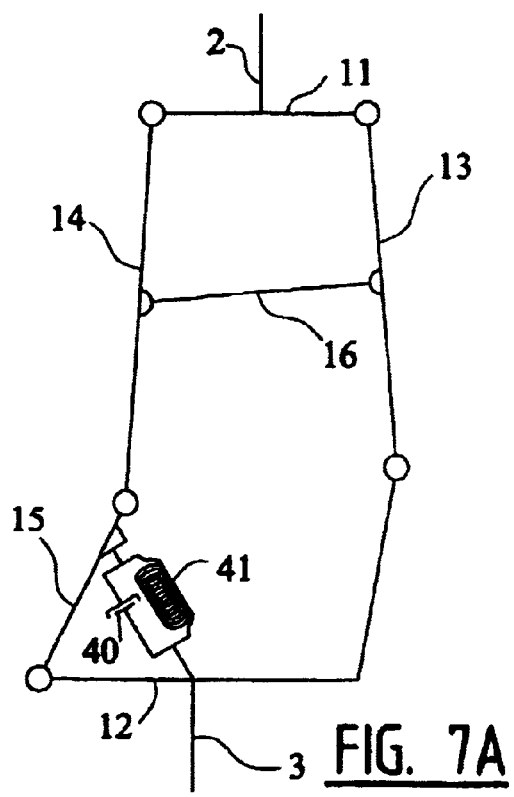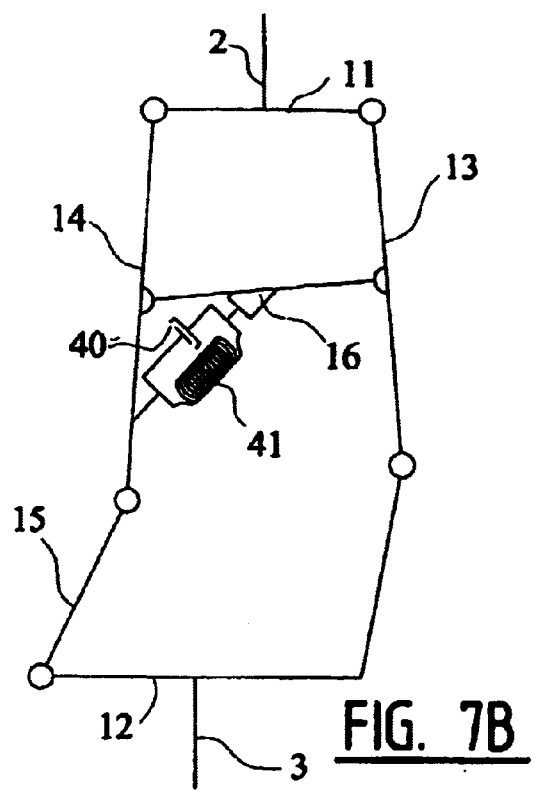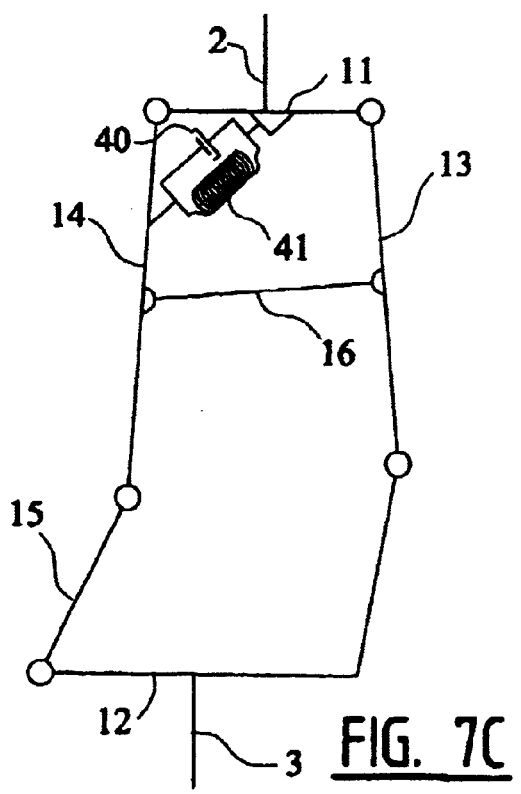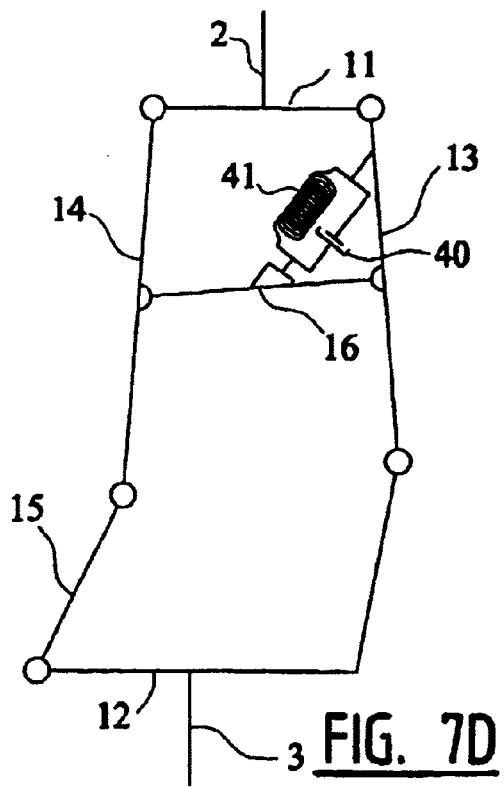

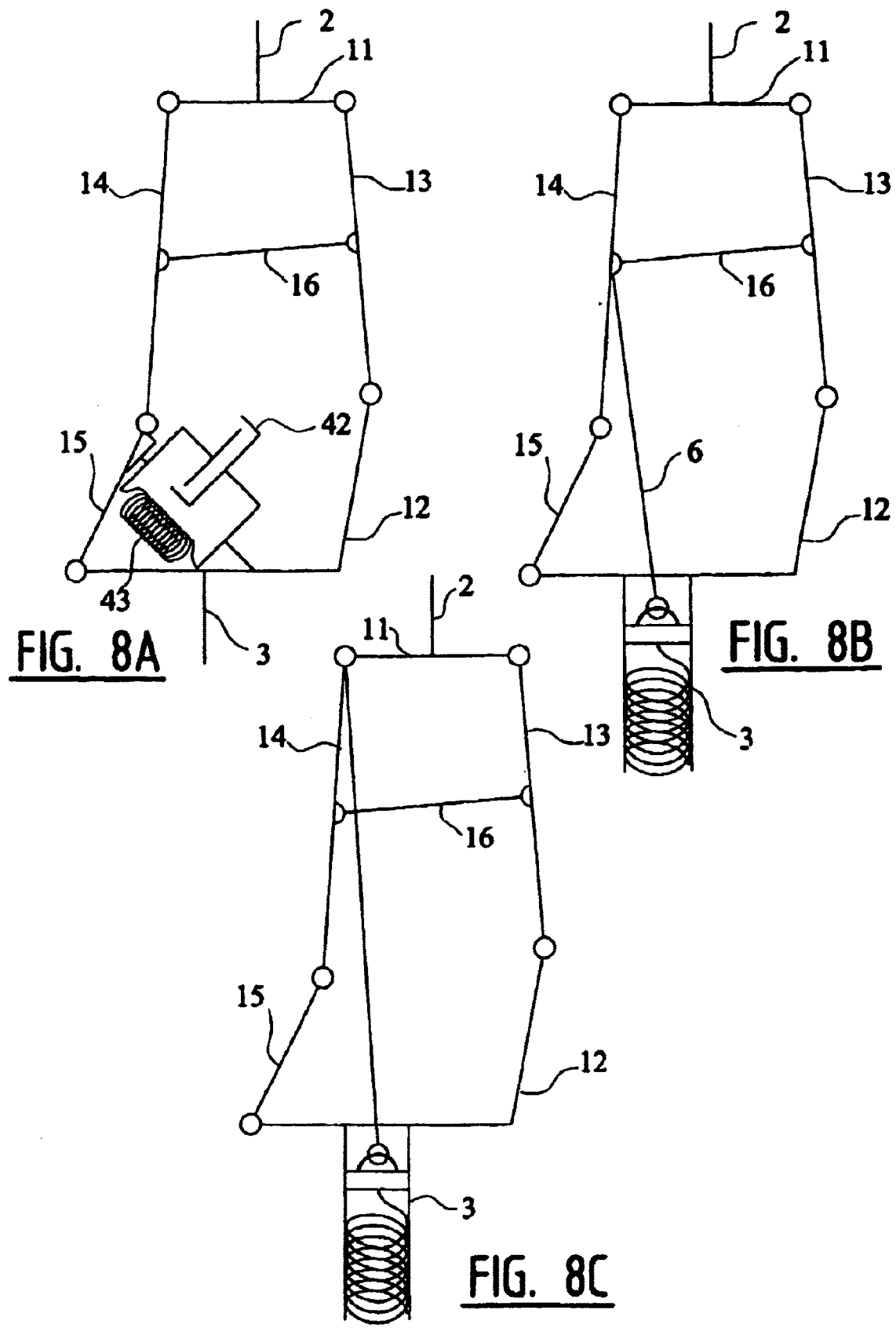

DEVICE FOR PIVOTABLY CONNECTING PARTS OF AN ORTHOPAEDIC DEVICE

Figure 5:
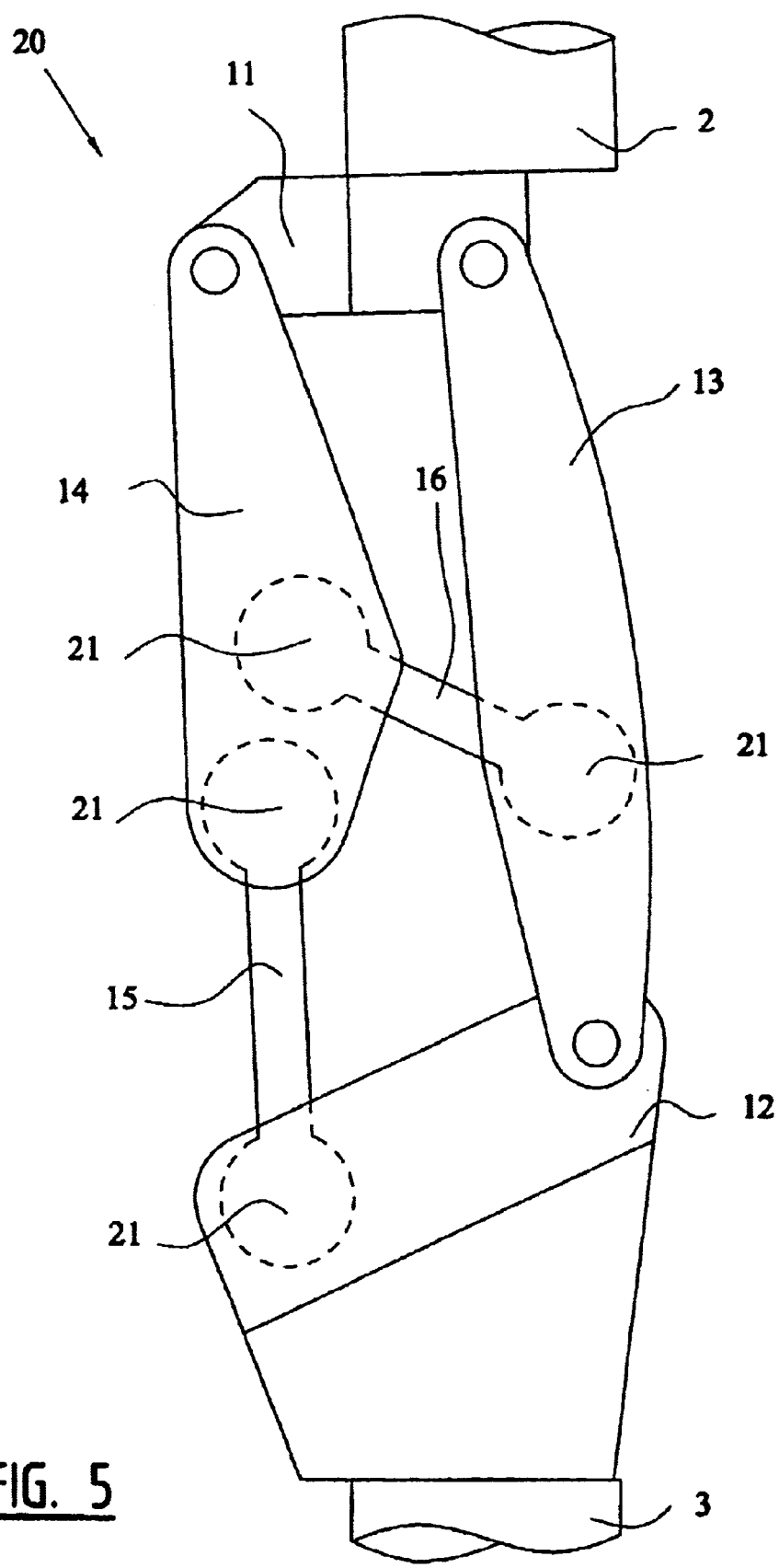

The invention relates to a device for pivotably connecting parts of an orthopaedic device, such as in particular a prosthetic knee for leg amputees.

The use of multibar mechanisms to replace or assist the joint function in orthopaedic devices has already been known for some time and is widely used on account of the advantages of a mechanism of this type over the more conventional mechanisms with one fixed pivot point. These advantages include, inter alia, better following or simulation of the natural movement of the limbs compared to a single-axis mechanism, and enhanced and more easily controllable stability of the mechanism when it is subject to load, and these advantages are achieved by suitable selection of the dimensions and the position of the bars of the mechanism with respect to one another. Particularly when a multibar mechanism is used to replace or assist the knee function, the latter factor is of great importance. This is because it is desirable, at the start of a step, when the mechanism is extended, the heel comes into contact with the ground and the mechanism is loaded by the weight of the user, for the mechanism not to start to pivot immediately, since this would not provide the user with any support, and consequently the user would fall over. In a single-axis mechanism, this can only be prevented by using a complex, relatively unreliable braking mechanism. By contrast, in a multibar mechanism this property can be achieved, for example, by selecting the geometry in such a way that, in the extended state of the mechanism, the virtual rotation point about which the lower leg or the lower-leg prosthesis pivots lies behind the line which connects the two points of load (the heel and the hip joint).

Moreover, by suitably selecting the geometry of the multibar mechanism, it is possible to achieve the effect whereby the virtual rotation point, at the end of a step, is located in such a way that the prosthesis or orthesis can more easily be made to execute a forwardly swinging movement than a single-axis mechanism. The high level of stability which can be achieved at the start of the step, the swinging-back movement which is easy to generate and the possibility of, in a simple way, finding a good compromise between these two properties make the multibar mechanism eminently suitable for replacing or supporting a joint function.

In applications of this nature, a kinematic multibar mechanism may exhibit initial yielding bending. This is desirable for some patients.

Particularly in what is known as a "knee disarticulation" (amputation of the leg at the joint), the existing devices have the drawback that the bending angle is insufficient. In addition, the thigh is unnaturally lengthened, which in the sitting position leads to an unnatural shape of the leg.

It is an object of the invention to provide a device which has the following characteristic features:

- adjustability in order, if desired, to obtain a high level of stability when load is applied to the heel,
- a decrease in the stability under front-foot loading at the end of the standing phase, so that the prosthesis can easily be made to swing,
- if appropriate, initial yielding, resulting in a damping action for the load on the prosthesis and therefore on the thigh stump,
- a very large maximum bending angle,
- a very minor lengthening in the position in which the prosthesis is bent through 90°,
- a cosmetically natural 90° position, and
- simplicity of design and reliability in use.

To this end, the invention provides a device, which device comprises a kinematic multibar mechanism with at least four bars, which bar mechanism allows a movement in the walking direction (L), in which device:

- a first bar can be connected to a first part of the orthopaedic device, such as a thigh socket,
- a second bar can be rigidly connected to a second part of the orthopaedic device, such as a lower-leg part,
- a third bar, which is arranged at the front as seen in the walking direction (L), is pivotably connected to the first bar and is pivotably connected to the second bar,
- a fourth bar, which is arranged behind the third bar as seen in the walking direction, is pivotably connected to the first bar and is pivotably connected to the second bar, in such a manner that the connection between the second bar and the fourth bar can be displaced along an imposed path, and
- a centre part of the fourth bar, lying between the two ends of the fourth bar, being connected to the third bar, in such a manner that the connection between the third bar and the centre part can be displaced along an imposed path.

A device of this type according to the invention provides the required functionality and a relatively high stance flexion in combination with limiting a second degree of freedom of movement, which is easy to achieve.

According to a preferred embodiment of the device according to the invention, the device comprises a fifth bar, which is pivotably connected to the fourth bar and to the second bar.

Another preferred embodiment of the device according to the invention comprises a sixth bar, which is pivotably connected to the fourth bar and to the third bar. The use of a fifth and sixth bar is preferred, since this creates a device which is of simple design and is reliable in use.

In yet another embodiment of the device according to the invention, at least one of the connections which can be displaced along an imposed path is a tongue-and-groove connection.

In this case, the imposed path may, if appropriate, be circular.

In a preferred embodiment of the device according to the invention, the pivot points between the sixth bar and the third and fourth bars lie at a distance from the ends of the third and fourth bars, respectively. It has been found that positioning the pivot points in this way allows the desired functionality to be achieved for a device which is used as knee pivot.

In yet another preferred embodiment of the device according to the invention, the device comprises spring means which are arranged between two bars of the multibar mechanism. The spring means can be used, for example, to facilitate moving the lower leg forward at the end of the swinging phase. In addition, the spring means may also comprise damping means. This enables energy to be dissipated in the swinging phase, so that the device moves smoothly into the extended position. This increases comfort for the user.

In one embodiment of the device according to the invention, the dimensions of the multibar mechanism are selected in such a manner that the device can be pivoted between the first, blocking position and a second position. The first, blocking position is intended to mean the position of the device in which stance flexion is achieved, while the second position is intended to mean the position of the device in which swing flexion is possible.

Preferably, the device is designed in such a manner that, during displacement of the vertical load on the device in the walking direction (L), the device pivots out of the blocked position into the second position. This allows natural walking when using the device.

In yet another preferred embodiment of the device according to the invention, the device comprises at least one stop for stopping a bar in order to define the blocking position. It is preferable for the stop to be adjustable. This allows the action and functionality of the device to be adjusted.

Furthermore, the device according to the invention may comprise spring means which act in the direction of the blocking position in order, at least in the blocking position of the device, to create a resilient action between the first part and the second part of the orthopaedic device. In this case, it is preferable for the stop to be made from a resilient material. As a result, in the blocking position there is a resilient action which increases comfort.

Finally, in an embodiment according to the invention, at least one of the bars may be of multiple design. This increases the torsional rigidity of the device.

Figure 6:
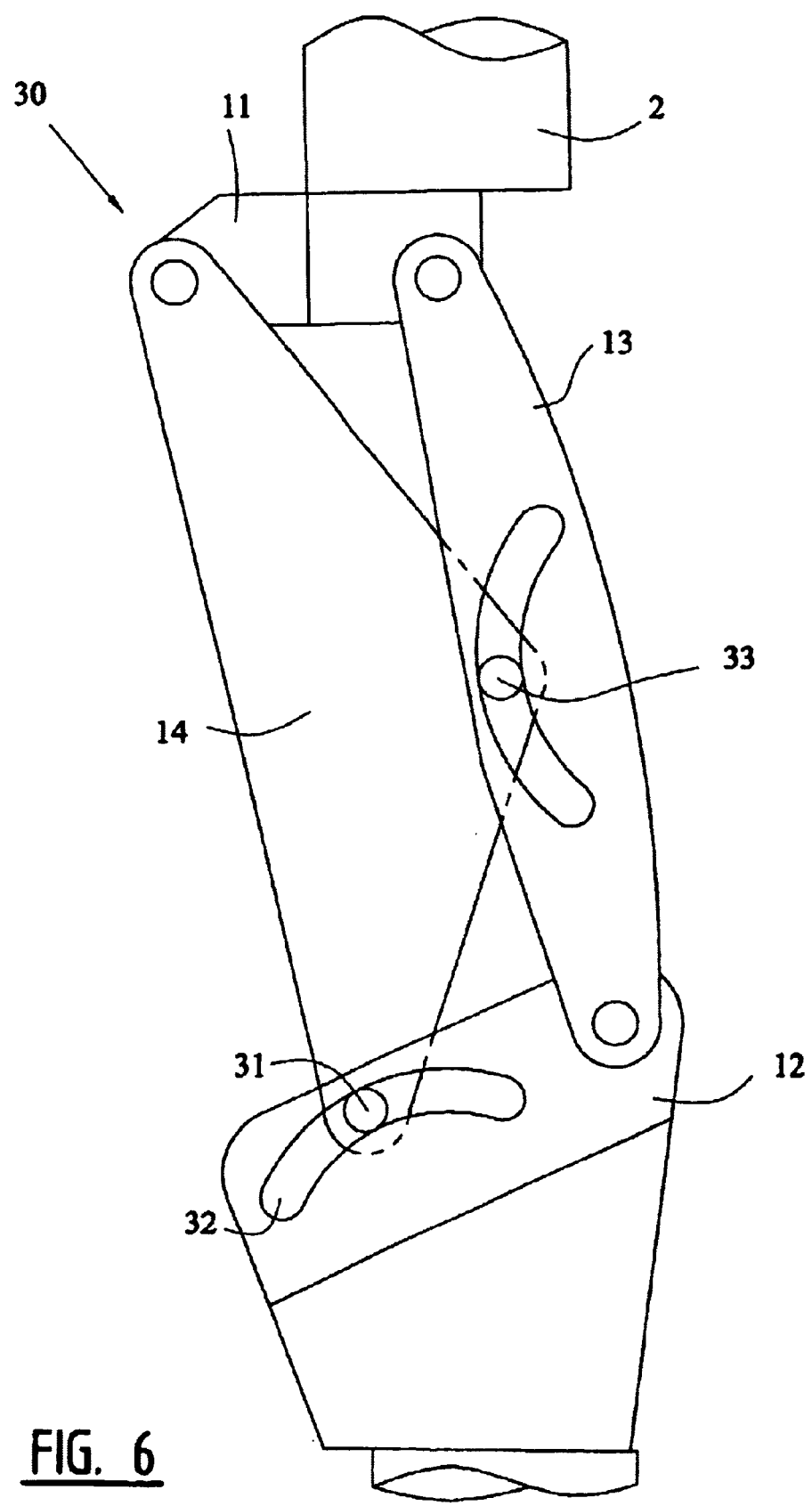

These and other characteristics of the device are explained in more detail with reference to the appended drawings, in which:

FIG. 1 shows a perspective view of a thigh prosthesis using a device according to the invention, in this case designed as a knee pivot, FIG. 2 shows a side view of the knee pivot shown in FIG. 1, FIGS. 3a–3c show three different positions of the knee pivot during a step, FIGS. 4a and 4b show the thigh prosthesis shown in FIG. 1 in the sitting position, FIG. 5 shows a second embodiment of a device according to the invention, FIG. 6 shows a third embodiment of the device according to the invention, FIGS. 7a to 7d diagrammatically depict various positions for fitting a resilient stop in a device according to the invention, FIGS. 8a–8c show various positions for fitting a resilient damper in a device according to the invention.

FIG. 1 shows a thigh prosthesis having a device according to the invention which is designed as a knee pivot 1. This knee pivot 1 comprises a multibar mechanism, in which means for securing to a thigh, such as a thigh socket 2, are arranged on the first bar 11. A lower-leg part 3 with an artificial foot 4 is arranged on a second bar 12 of the knee pivot 1.

FIG. 2 shows the knee pivot 1 according to the invention in more detail. It can be seen once again that the first bar 11 of the multibar mechanism is connected to the thigh socket 2 and that the second bar 12 is connected to the lower-leg part 3. In the walking direction L, a third bar 13 is arranged pivotably at the front side between the first bar 11 and the second bar 12. Furthermore, a fourth bar 14 and a fifth bar 15 are arranged behind the third bar 13, as seen in the walking direction L, which fourth and fifth bars 14, 15 are pivotably connected to one another on one side and on the other side are pivotable connected to the first bar 11 and the second bar 12, respectively.

Finally, a sixth bar 16 is arranged pivotably between the third bar 13 and the fourth bar 14. The pivot points 17 and 18 of this sixth bar lie at a distance from the ends of the third bar 13 and the fourth bar 14, respectively. The ends of these bars 13 and 14 are understood to mean the pivot points arranged at these ends. Furthermore, in the knee pivot 1 there is a damper 5, which is connected, by means of a piston rod 6, to one of the bars of the bar mechanism, in this case to a fourth bar 14.

A stop 19 is fitted in order to limit the travel of the bar 15.

The operation of the knee joint 1 according to the invention is explained in more detail with reference to FIGS. 3a to 3c.

FIG. 3a shows the position of the knee pivot 1 when the thigh prosthesis is at the start of the step, i.e. the position in which the artificial foot 4 is situated in front of the other foot. The vertical load B acting on the knee joint 1 lies behind the knee joint 1, as seen in the walking direction L. The fifth bar 15, and therefore the entire mechanism, is now in the blocked position, with the result that the knee pivot 1 is fixed and the thigh prosthesis can commence the step.

FIG. 3b shows the position in which the vertical load B acting on the knee joint 1 has shifted to in front of the knee joint 1. This position preferably corresponds to the situation in which the vertical load vector B intersects the front side of the artificial foot 4. This corresponds to the situation in which the user is standing on the "ball of the foot". At this moment, the fifth bar 15 pivots out of the blocked position, as shown in FIG. 3a, into a second position.

FIG. 3c shows the fifth bar 15 in the second position, so that the lower-leg part 3 can enter the swinging phase. At this time, the artificial foot 4 is no longer in contact with the ground and the thigh prosthesis can be swung into the position which correspond to that shown in FIG. 3a.

FIGS. 4a and 4b show the sitting position of the knee pivot 1. A characteristic feature of the knee pivot 1 according to the invention is that, in the sitting position of the device, it adopts a shape which is such that the appearance of the leg with the prosthesis corresponds to that of a leg without prosthesis. It is clearly evident from FIG. 4b that the third bar 13 of the knee joint 1 runs virtually parallel to the front side of the lower-leg part 3.

FIG. 5 shows a second embodiment 20 of a device according to the invention. This device largely corresponds to the knee pivot 1 shown in FIG. 1. Therefore, identical parts are provided with identical reference numerals. It is clearly apparent that a first bar 11 is connected to a thigh prosthesis, while a second bar 12 is connected to a lower-leg part 3. A third bar 13, which is pivotably connected at each end, runs between this first bar 11 and second bar 12. Furthermore, a fourth bar 14 is arranged pivotably on the first bar 11, the other end of which fourth bar 14 is pivotably connected to a fifth bar 15, which in turn is connected to the second bar 12. Also, a sixth bar 16 runs between the fourth bar 14 and the third bar 13.

The difference from the device shown in FIG. 1 is that, instead of pivot pins, in this case ball-and-socket joints 21 are used to pivotably connect the fifth bar 15 and the sixth bar 16. The advantage of these ball-and-sockets joints is that the mechanism will still operate despite any manufacturing tolerances. In fact, if a device 1 as shown in FIG. 1 is not manufactured with sufficient accuracy, there is a risk that the mechanism will fail to operate entirely.

FIG. 6 shows a third embodiment of a device according to the invention. In this case too, identical parts are denoted by identical reference numerals. The difference from the two embodiments 1 and 20 above is that there are no fifth and sixth bars. Instead, the fourth bar 14 is connected to the second bar 12 by means of a tongue-and-groove connection. This tongue-and-groove connection comprises a tongue 31, which is arranged at the end of the fourth bar 14, and a curved groove 32 arranged in the second bar 12.

Furthermore, the fourth bar 14 is connected to the third bar 13 by means of a tongue-and-groove connection. For this purpose, a second tongue 33 is arranged on a centre part of the fourth bar 14 and runs in a groove 34 arranged in the third bar 13.

It will be obvious that where the tongues 31 and 33 are arranged, they may be replaced by a groove, while the grooves 32, 34 are replaced by a tongue.

FIGS. 7a to 7d diagrammatically depict a device which corresponds to the knee pivot 1 shown in FIG. 1. Therefore, identical parts are once again denoted by identical reference numerals. These four figures show four different positions for a resilient stop which comprises a stop part 40 and a resilient element 41. As is shown in the figures, this resilient stop may, for example, be arranged between the second bar 12 and the fifth bar 15 (FIG. 7a), between the fourth bar 14 and the sixth bar 16 (FIG. 7b), between the first bar 11 and the fourth bar 14 (FIG. 7c) or between the third bar 13 and the sixth bar 16 (FIG. 7d). However, the design shown in FIG. 7a is preferred.

FIGS. 8a to 8c show various positions for a resilient damper. In this case too, the bar mechanism corresponds to the mechanism of the device shown in FIG. 1, and therefore identical parts are once again denoted by identical reference numerals. The resilient damper is diagrammatically indicated by a damping element 42 and a spring 43. This assembly 42, 43 may, for example, be positioned between the second bar 12 and fifth bar 15 (FIG. 8a), the fourth bar 14 and the second bar 12 or with the lower-leg part 3 arranged fixedly thereon (FIGS. 8b and 8c). The diagrammatic structure shown in FIG. 8b corresponds to the knee pivot shown in FIG. 1 and is therefore preferred.

What is claimed is:

1. Device for pivotably connecting parts of an orthopaedic device, such as in particular a prosthetic knee for leg amputees, which device comprises a kinematic multibar mechanism with at least four bars, which bar mechanism allows a movement in the walking direction (L), in which device a first bar can be connected to a first part of the orthopaedic device, such as a thigh socket, a second bar can be rigidly connected to a second part of the orthopaedic device, such as a lower-leg part, a third bar, which is arranged at the front as seen in the walking direction (L), is pivotably connected to the first bar and is pivotably connected to the second bar, the third bar running between the first bar and the second bar, a fourth bar, which is arranged behind the third bar as seen in the walking direction, is pivotably connected to the first bar and is pivotably connected to the second bar, in such a manner that the connection between the second bar and the fourth bar can be displaced along an imposed path, and a centre part of the fourth bar, lying between the two ends of the fourth bar, being connected to the third bar, in such a manner that the connection between the third bar and the centre part can be displaced along an imposed path.

2. Device according to claim 1, wherein the device comprises a fifth bar, which is pivotably connected to the fourth bar and to the second bar.

3. Device according claim 1, wherein the device comprises a sixth bar, which is pivotably connected to the fourth bar and to the third bar.

4. Device according to claim 1, in which at least one of the connections which can be displaced along an imposed path is a tongue-and-groove connection.

5. Device according to claim 1, in which the imposed path is a circular path.

6. Device according to claim 3, in which the pivot points between the sixth bar and the third and fourth bars lie at a distance from the ends of the third and fourth bars, respectively.

7. Device according to claim 1 comprising spring means which are arranged between two bars of the multibar mechanism.

8. Device according to claim 7, in which the spring means comprise damping means.

9. Device according to claim 1, in which the dimensions of the multibar mechanism are selected in such a manner that the device can be pivoted between a first, blocking position and a second position.

10. Device according to claim 9, in which, when the vertical load of the device is displaced in the walking direction (L), the device pivots out of the blocked position into the second position.

11. Device according to claim 9, comprising at least one stop for stopping a bar so as to define the blocking position.

12. Device according to claim 11, in which the stop is adjustable.

13. Device according to claim 9, comprising spring means, which act in the direction of the blocking position, for creating, at least in the blocking position of the device, a resilient action between the first part and the second part of the orthopaedic device.

14. Device according to claim 11, in which the stop comprises a resilient material.

15. Device according to claim 1, in which at least one of the bars is of multiple design.

* * * * *